United States Patent [19]

Hearon et al.

[11] 4,016,207
[45] Apr. 5, 1977

[54] HYDROLYZING DI- AND TRICARBOXY CELLULOSES WITH SULFUROUS ACID

[75] Inventors: William Montgomery Hearon, Portland, Oreg.; John F. Witte; Cheng Fan Lo, both of Vancouver, Wash.

[73] Assignee: Boise Cascade Corporation, Boise, Idaho

[22] Filed: Nov. 5, 1975

[21] Appl. No.: 628,887

[52] U.S. Cl. .............................................. 260/528
[51] Int. Cl.² ........................................ C07C 51/00
[58] Field of Search .................................. 260/528

[56] References Cited
UNITED STATES PATENTS 2,973,387   2/1961   Van Clive et al. ............... 260/602

OTHER PUBLICATIONS

Head, *J. Chem. Soc.,* pp. 1135–1136, (1948).
Mehltretter et al., *I ɜ EC Product Research and Development* vol. 1, No. 1, pp. 62–64, (1962).

*Primary Examiner*—Jane S. Myers
*Attorney, Agent, or Firm*—Eugene D. Farley

[57] ABSTRACT

Di- and tricarboxy celluloses are hydrolyzed with sulfurous acid in an aqueous medium to a mixture of erythronic acid and glyoxylic acid, in the case of dicarboxy cellulose; to a mixture of meso tartaric acid and glyoxylic acid in the case of tricarboxy cellulose; and to a mixture of these three products, in the case of a feedstock comprising a mixture of di- and tricarboxy celluloses.

8 Claims, No Drawings

HYDROLYZING DI- AND TRICARBOXY CELLULOSES WITH SULFUROUS ACID

BACKGROUND AND BRIEF STATEMENT OF THE INVENTION

This invention relates broadly to a process for obtaining valuable commercial chemical products from wood and woody materials. It pertains particularly to a process for obtaining high yields of substantially pure erythronic acid, meso tartaric acid and glyoxylic acid by the sulfurous acid hydrolysis of di- and tricarboxy celluloses and mixtures thereof. Erythronic acid, meso tartaric acid and glyoxylic acid are useful organic chemicals.

Erythronic acid is a highly water soluble organic acid useful, for example, in the manufacture of polyurethane foams and as an intermediate in the processes of the synthetic organic chemical industry.

Meso tartaric acid is of significance commercially since it is useful as a substitute for the tartaric acid of commerce as a component of lacquers and textile printing inks, and also as a complexing material for metallic ions.

Glyoxylic acid has important commercial applications in pharmaceuticals, cosmetics, photographic chemicals, agricultural chemicals and electroplating mixtures.

As will be described more fully hereinafter, it is possible to manufacture these three acids from wood and woody materials by (1) converting the wood or woody material to cellulose, e.g. paper pulp, (2) oxidizing the cellulose to dialdehyde cellulose, (3) oxidizing the dialdehyde cellulose to di- and tricarboxy celluloses, and (4) hydrolyzing the di- and tricarboxy celluloses to erythronic, meso tartaric and glyoxylic acids.

Although it heretofore in theory has been possible to carry out the above synthetic sequence, in practice a major barrier has been the difficulty of carrying out the hydrolytic reactions whereby the di- and tricarboxy celluloses are hydrolyzed to the acids in question. The di- and tricarboxy celluloses, like many cellulose derivatives, are sensitive to reaction with various chemical reagents and convert readily to complex mixtures which contain various degradation products of cellulose. Such products include tarry materials, colored products, and degradation products of low molecular weight.

It accordingly is the general object of the present invention to provide a process for the conversion of di- and tricarboxy celluloses to substantially pure erythronic, meso tartaric and glyoxylic acids in high yields, i.e. in yields of the order of 97% of the theoretical, at relatively low cost, and on a large commercial scale.

We now have discovered, and it is the essence of the present invention, that when sulfurous acid is included in the hydrolytic reaction mixture used for hydrolyzing di- and tricarboxy celluloses to erythronic, meso tartaric and glyoxylic acids, it acts as a unique catalyst in accomplishing the substantially complete conversion of the carboxy cellulose feedstock to derivative acid products in pure form, and in a form in which they may be isolated readily from the reaction mixture and separated from each other.

Broadly stated therefore, the process of the present invention comprises first forming a suspension in aqueous sulfurous acid of a carboxy cellulose-containing feedstock of the class consisting of dicarboxy cellulose, tricarboxy cellulose and mixtures thereof and thereafter treating the carboxy cellulose feedstock with the aqueous sulfurous acid at a temperature and for a time predetermined to hydrolyze the dicarboxy cellulose content of the feedstock to erythronic acid and glyoxylic acid and the tricarboxy cellulose content thereof to meso tartaric acid and glyoxylic acid.

This beneficial behavior of sulfurous acid is in marked contrast to the behavior of other acidic materials when it is attempted to use them as catalysts for the hydrolytic conversion of di- and tricarboxy celluloses to the indicated acid products. For example, when it is attempted to use sulfuric acid, hydrochloric acid, phosphoric acid and the like a certain proportion of the carboxy acid feedstock is converted to the desired organic acid products. However, the yields are low, the product is dark in color, and there are present tarry and syrupy materials which make impossible isolation of the desired organic acid products in a pure condition.

DESCRIPTION OF SPECIFIC EMBODIMENTS OF THE INVENTION

As indicated above, the ultimate starting material for the hereindescribed process of hydrolyzing di- and tricarboxy cellulose comprises cellulose itself. In particular, there may be used papermill primary sludges consisting essentially of bleached pulp and clay, which sludges are a substantially valueless byproduct of the papermaking industry and are available in enormous quantities at substantially no cost. There also may be used as ultimate starting materials such low cost products as various papermill pulps, cotton linters and the like.

The feedstock used in the presently described process is prepared from the foregoing or other cellulose starting materials by first oxidizing them to dialdehyde cellulose in known manner. Dialdehyde cellulose contains aldehyde groups in the two and three positions in the cellulose structural unit. It contains a primary alcohol group in the number six position.

The dialdehyde cellulose containing these reactive functional groups may be oxidized stepwise, also in known manner, by oxidizing agents such as nitrogen tetroxide. In the first step of the oxidative reaction, the relatively reactive aldehyde groups are oxidized to carboxyl groups, thereby forming dicarboxy cellulose (2, 3- dicarboxy cellulose). In the second step of the oxidative reaction the less reactive primary alcohol group is oxidized to a carboxyl group, thereby forming tricarboxy cellulose (2,3,6 - tricarboxy cellulose).

In the production of one or the other of these carboxy celluloses there may be, and usually is, produced a final product consisting of variable proportions of both di- and tricarboxy celluloses. Thus when the production of tricarboxy cellulose is contemplated, and the oxidation is carried out under conditions as strenuous as it is possible to use without further degrading the dialdehyde cellulose to products other than carboxy celluloses, the tricarboxy cellulose products will contain preponderantly the desired tricarboxy cellulose, but also from 10 to 20% of dicarboxy cellulose.

The relative proportions of di- and tricarboxy celluloses in the oxidation product may be determined quite accurately by determining the carboxyl content of the product. If the product is pure dicarboxy cellulose it will have a carboxyl content of 46.88%. If it is pure tricarboxy cellulose, it will have a carboxyl content of 65.53%. Intermediate values of carboxyl content indicate a mixture of these two products in amounts corresponding to the intermediate carboxyl content.

It is the dicarboxy cellulose and the tricarboxy cellulose or mixtures thereof prepared in the foregoing or other suitable manners that comprise the feedstock for the hereindescribed process.

The hydrolysis of the carboxy celluloses is autocatalytic since they are themselves weakly acidic in properties. However, their autocatalytic conversion does not lead to a useful result. The yields of the desired acid products are low and the products are impure.

In effectuating the process there first is formed a suspension of the carboxy cellulose feedstock in aqueous sulfurous acid. In the usual manner of proceeding, this is accomplished by suspending the carboxy cellulose in water and then bubbling sulfur dioxide into the aqueous suspension until the desired amount of sulfurous acid has been formed.

The amount of sulfurous acid employed as the hydrolysis catalyst may be varied within wide limits depending upon the other operating conditions including especially the temperature and pressure of reaction. We have found that the addition of even small amounts of sulfurous acid leads to the provision of a workable process producing pure products in high yields. In practice, however, the aqueous sulfurous acid should contain at least about 0.8% by weight sulfurous acid at the beginning of the reaction. The upper limit is determined by practical considerations such as the need to recover and recycle large quantities of sulfur dioxide.

Practically considered, there is no advantage to including a large proportion of sulfur dioxide in the reaction mixture. Since the reaction is catalytic, but a relatively small amount is required. Although excess sulfur dioxide does not exert a harmful effect, in working up the reaction mixture any excess sulfur dioxide must be removed and recovered for recycling, thereby somewhat complicating the procedure.

We have found that high concentrations of sulfur dioxide, e.g. concentrations of the order of 5% by weight, do not act to increase the yield of the desired products. Neither do they act to reduce the time of the reaction, nor to improve the quality of the product.

In general the upper limit of use of the sulfurous acid is that amount required to saturate the aqueous suspension medium with sulfur dioxide under the temperature-pressure conditions under which the reaction is to be carried out. If the reaction medium is prepared at a standard pressure of 760 mm., at 0° C., 22.83 grams of sulfur dioxide are required to saturate 100 grams of water. At 20° C., 11.28 grams are required, and at 40° C., 4.1 grams of sulfur dioxide are required for the same purpose. These amounts, as well as lesser amounts down to those required to make a 0.8% by weight solution of sulfurous acid may be used to achieve the desired result. Preferably the reaction medium at the beginning of the reaction should contain at least 2% by weight of sulfurous acid.

Although the desired hydrolytic conversions will occur at temperatures of below 100° C., they occur much more rapidly at temperatures of from 100° to 200° C., preferably from 105° to 150° C. At these temperatures the solubility of sulfur dioxide in water is substantially zero at atmospheric pressure.

Accordingly, to provide sulfurous acid of effective concentration, at these elevated temperatures, the hydrolysis should be carried out under pressure. Then when the reaction mixture is heated, the sulfur dioxide distributes itself between the gaseous and liquid phases until an equilibrium is established.

The pressure employed is that at which a catalytic amount of sulfurous acid is present in the reaction medium. For convenience and efficiency of operation, it is preferred to carry out the reaction in a substantially sealed reactor. The pressure developed then will be that prevailing in a sealed reactor at the temperature of operation.

The time required to effect the hydrolytic conversion of the carboxy acids to the desired organic acid products is determined by such factors as the concentration of the sulfurous acid employed, the operating temperature and the operating pressure. In general, however, the reaction requires but a short time, for example a time of from 1 to 8 hours.

In a typical procedure, the carboxy cellulose feedstock is placed in a sealed reactor with the selected amount of sulfurous acid and heated for from 1 to 8 hours at the selected temperature. At the end of this time the reaction mixture usually is pale yellow. The reactor pressure is released, the reaction mixture removed from the reactor, and cooled to substantially ambient temperature. It then is diluted with water and boiled for the removal of sulfur dioxide which may be recovered and recycled. The reaction mixture then is fractionated in suitable manner for the separation of its component products, i.e. erythronic, meso tartaric and glyoxylic acids.

EXAMPLES

The process of the present invention for converting di- and tricarboxy celluloses to erythronic, meso tartaric and glyoxylic acid is illustrated by the following examples:

EXAMPLE 1

The feedstock used in this example was tricarboxy cellulose obtained by the nitrogen tetroxide oxidation of dialdehyde cellulose. It contained 61.8% carboxyl, indicating a content of 78.84% tricarboxy cellulose and 21.16% dicarboxy cellulose.

10 Grams of the carboxy cellulose feedstock and 5.5% by weight of freshly prepared sulfurous acid (100 ml.) were placed in a sealed reactor and heated at 125° to 130° C. for 3.5 hours. The reaction mixture then was cooled, the pressure released from the reactor, and the reaction product removed, in the form of a pale yellow solution.

The cooled reaction product was diluted with 100 ml. water and boiled for the removal of sulfur dioxide until the vapors were neutral to litmus paper. It then was fractionated into its orgainic acid component products. It yielded 6.07 grams of meso tartaric acid monohydrate (93.0% of theory). This product had a neutralization equivalent of 84.5 (theory 84) and had a melting point of 159° C. which was not depressed by admixture with authentic meso tartaric acid monohydrate.

Further fractionation of the reaction mixture produced a 92% yield of glyoxylic acid. The erythronic acid product was present in relatively small amounts, since only 21.16% by weight of its dicarboxy cellulose parent material was present in the original feedstock. The amount produced, however, was present as a water soluble component of the mixture after removal of the meso tartaric and glyoxylic acids.

EXAMPLE 2

This example illustrates the process of the present invention using varying amounts of sulfurous acid catalyst.

The general procedure of Example 1 was followed using in each instance 2.5 grams of carboxy cellulose feedstock in 30 ml. of sulfurous acid reaction medium. The carboxy cellulose feedstock had a carboxyl content of 58.5%, corresponding to 60.63% tricarboxy cellulose and 39.37% dicarboxy cellulose. It contained 2.6063 carboxyl groups per glucose unit and had a molecular weight of 200.5.

In each instance, the reaction mixture was heated to and maintained at 120° C. for seven hours. The meso tartaric acid product was converted to calcium meso tartaric acid monohydrate, and the glyoxylic acid product to calcium glyoxylate hemihydrate. The results were as follows:

| Concentration of $H_2SO_3$ | Calcium Meso tartrate Monohydrate | | Calcium Glyoxylate Hemihydrate | |
|---|---|---|---|---|
| | Grams | % of Theory | Grams | % of Theory |
| 0 | 0.9985 | 64.1% | 0.0865 | 6.8% |
| 0.1% | 0.9324 | 59.9 | 0.2912 | 22.9 |
| 0.5 | 0.9400 | 60.4 | 0.3180 | 25.0 |
| 1.0 | 1.3370 | 85.9 | 0.7737 | 60.8 |
| 3.0 | 1.4345 | 92.1 | 1.0531 | 82.8 |
| 4.0 | 1.3872 | 89.1 | 1.0610 | 83.4 |
| 22.0 | 1.4086 | 90.5 | 1.0219 | 80.4 |

| Concentration of $H_2SO_3$ | Color of Hydrolysate | Color of Calcium Meso Tartrate Monohydrate | Color of Calcium Glyoxylate Hemihydrate |
|---|---|---|---|
| 0 | Deep brown | Brown | Grey |
| 0.1 | Deep brown | Brown | Grey |
| 0.5 | Deep brown | Brown | Grey |
| 1.0 | Light brown | White | White |
| 3.0 | Yellowish brown | White | White |
| 4.0 | Pale yellow | White | White |
| 22.0 | Pale yellow | White | White |

EXAMPLE 3

This example illustrates the unsatisfactory nature of the reaction occurring when it is attempted to hydrolyse the di- and tricarboxy celluloses to their derivative organic acids, using hydrochloric acid as a catalyst.

The feedstock employed for this example was tricarboxy cellulose prepared by the nitrogen tetroxide oxidation of dialdehyde cellulose. It had a carboxyl content of 58.50% and contained 2.6063 carboxyls per glucose unit. Its molecular weight was 200.49. This indicates a tricarboxy cellulose content of 60.63% and a dicarboxy cellulose content of 39.37%.

5 Grams of the feedstock was placed in 150 ml. of 4% hydrochloric acid and refluxed for 12 hours. At the end of this time the reaction mixture was cooled and the cooled hydrolysate, which was dark brown in color, was fractionated for separation of meso tartaric acid. The latter was obtained as an impure brown solid. Its mixed melting point with a known sample of meso tartaric acid monohydrate was depressed by 5° C.

The reaction mixture after removal of the meso tartaric acid was fractionated for removal of its content of glyoxylic acid. This product was obtained in a yield of but 32.81% of theory.

EXAMPLE 4

This example illustrates the unsatisfactory character of the sulfuric acid-catalyzed hydrolytic conversion of the di- and tri- carboxy celluloses to their derivative organic acids.

The tricarboxy cellulose feedstock employed in this example had a carboxyl content of 61.06% by weight, a molecular weight of 202.46 and carboxy group per glucose unit analysis of 2.7482. This indicated a content of tricarboxy cellulose of 74.82% and of dicarboxy cellulose of 25.18%.

10 Grams of the tricarboxy cellulose was placed in a sealed bomb with 100 ml. of 6.56% by weight sulfuric acid. The reaction mixture was heated at 110° to 115° C. for 16 hours. After two hours the mixture started to darken. It became progressively darker during the reaction period.

The reaction vessel was cooled, the pressure released and the reaction mixture, which was dark brown in color, was discharged. It was fractionated in the usual manner, whereupon a yield of 72.15% of theory of impure meso tartaric acid monohydrate was obtained.

The reaction mixture was fractionated further for the recovery of its content of glyoxylic acid. This material was recovered in amount of 4.27% of theory. In both cases the products were impure and dark in color.

The above procedure was repeated using 100 ml. of 6.56% by weight sulfurous acid. After 16 hours the nearly colorless reaction mixture was worked up and yielded 92.7% of theory of pure meso tartaric acid monohydrate and 78.5% of theory of colorless glyoxylic acid.

Having thus described our invention in preferred embodiments, we claim:

1. The process which comprises: a. forming a suspension in aqueous sulfurous acid containing from 0.8% by weight to that amount required to saturate the aqueous suspension with sulfurous acid under the temperature pressure conditions of the treating reaction of a carboxy cellulose-containing feedstock of the class consisting of 2,3-dicarboxy cellulose, 2,3,6-tricarboxy cellulose, and mixtures thereof and b. treating the carboxy cellulose feedstock with the aqueous sulfurous acid at a temperature of from 100° to 200° C. for a time predetermined to hydrolyze 2,3-dicarboxy cellulose content of the feedstock to erythronic acid and glyoxylic acid and the 2,3,6-tricarboxy cellulose content thereof to meso tartaric acid and glyoxylic acid.

2. The process of claim 1 wherein the carboxy cellulose-containing feedstock consists essentially of 2,3-dicarboxy cellulose.

3. The process of claim 1 wherein the carboxy cellulose-containing feedstock consists essentially of 2,3,6-tricarboxy cellulose.

4. The process of claim 1 wherein the aqueous sulfurous acid contains from 2% by weight to that amount required to saturate the aqueous suspension medium with sulfurous acid under the temperature-pressure conditions of the treating reaction.

5. The process of claim 1 including the step of effectuating the treatment with sulfurous acid under predetermined conditions of superatmospheric pressure and elevated temperature.

6. The process of claim 1 including the step of carrying out the treatment with sulfurous acid in a substantially sealed reactor at a temperature of from 100° to 200° C. and corresponding pressures.

7. The process of claim 1 including the step of carrying out the treatment with sulfurous acid in a substantially sealed reactor at a temperature of from 105° to 150° C. and corresponding pressures.

8. The process which comprises:
a. forming in aqueous sulfurous acid a suspension of a carboxy cellulose-containing feedstock of the class consisting of 2,3-dicarboxy cellulose, 2,3,6-tricarboxy cellulose and mixtures thereof,
b. the aqueous sulfurous acid containing from 2% by weight sulfurous acid to that amount required to saturate the aqueous suspension medium with sulfurous acid under the temperature-pressure conditions of the treating reaction, and
c. reacting the feedstock with the aqueous sulfurous acid in a substantially sealed reactor at a temperature of from 105° to 150° C. and corresponding pressures for a time sufficient to convert the feedstock to high yields of erythronic and glyoxylic acids, in the case of 2,3-dicarboxy cellulose; of meso tartaric and glyoxylic acids in the case of 2,3,6-tricarboxy cellulose and to erythronic, glyoxylic and meso tartaric acids in the case of a mixture of 2,3-di- and 2,3,6-tricarboxy celluloses.

* * * * *